United States Patent
Boser et al.

(10) Patent No.: US 10,820,888 B2
(45) Date of Patent: Nov. 3, 2020

(54) MINIATURE ULTRASONIC IMAGING SYSTEM

(71) Applicant: THE REGENTS OF THE UNIVERSITY OF CALIFORNIA, Oakland, CA (US)

(72) Inventors: Bernhard E. Boser, Berkeley, CA (US); David A. Horsley, Albany, CA (US); Hao-Yen Tang, Berkeley, CA (US); Yipeng Lu, Davis, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 1232 days.

(21) Appl. No.: 15/065,621

(22) Filed: Mar. 9, 2016

(65) Prior Publication Data

US 2016/0262725 A1 Sep. 15, 2016

Related U.S. Application Data

(60) Provisional application No. 62/130,778, filed on Mar. 10, 2015.

(51) Int. Cl.
*A61B 8/00* (2006.01)
*A61B 8/04* (2006.01)
(Continued)

(52) U.S. Cl.
CPC .............. *A61B 8/4483* (2013.01); *A61B 8/04* (2013.01); *A61B 8/06* (2013.01); *B06B 1/0662* (2013.01); *A61B 8/5207* (2013.01)

(58) Field of Classification Search
CPC .......... A61B 8/04; A61B 8/06; A61B 8/4483; A61B 8/5207; B06B 1/0662
See application file for complete search history.

(56) References Cited

U.S. PATENT DOCUMENTS

| 2011/0028845 A1* | 2/2011 | Haider | A61B 8/0883 |
|---|---|---|---|
| | | | 600/459 |
| 2013/0079642 A1* | 3/2013 | Marshall | A61B 8/12 |
| | | | 600/463 |

(Continued)

OTHER PUBLICATIONS

Wagner, Dale, R, "Ultrasound as a Tool to Assess Body Fat", Journal of Obesity (Year: 2013).*

(Continued)

*Primary Examiner* — Christopher L Cook
(74) *Attorney, Agent, or Firm* — O'Banion & Ritchey LLP; John P. O'Banion

(57) ABSTRACT

An ultrasonic imaging apparatus having a Micro-machined Ultrasonic Transducer (MUT), such as a Piezoelectric MUT (PMUT) or Capacitive MUT (CMUT), with a transmitting mode and a receiving mode for generating and sensing acoustic pressure in imaging applications. During transmission in a PMUT the inverse piezoelectric effect on the piezo layer causes transverse stress, which causes a bending moment in the PMUT structure leading to out-of-plane deflection. Different applied signs of voltage generates different signs of stress inside the piezo that in turn cause oscillating motion generating an acoustic pressure wave. During signal reception, incident pressure waves deflect the PMUT creating transverse stress, resulting in a charge determined through measuring voltage between electrodes. The apparatus is particularly well-suited for use in health care, such as measuring fat/muscle thickness, blood-flow, and blood pressure.

25 Claims, 8 Drawing Sheets

(51) Int. Cl.
*A61B 8/06* (2006.01)
*B06B 1/06* (2006.01)
*A61B 8/08* (2006.01)

(56) References Cited

U.S. PATENT DOCUMENTS

| | | | | |
|---|---|---|---|---|
| 2013/0310691 A1* | 11/2013 | Furman | .................... | A61B 8/06 600/447 |
| 2015/0057540 A1* | 2/2015 | Sameshima | ............... | B06B 1/06 600/437 |
| 2016/0066881 A1* | 3/2016 | Li | ........................... | A61B 8/12 600/443 |

OTHER PUBLICATIONS

Lu et al., "High Frequency Piezoelectric Micromachined Ultrasonic Transducer Array for Intravascular Ultrasound Imaging", IEEE International Conf. on Micro Electro Mechanical Systems (MEMS), Jan. 2014 (Year: 2014).*

* cited by examiner

MINIATURE ULTRASONIC IMAGING SYSTEM

CROSS-REFERENCE TO RELATED APPLICATIONS

This application claims priority to, and the benefit of, U.S. provisional patent application Ser. No. 62/130,778 filed on Mar. 10, 2015, incorporated herein by reference in its entirety.

INCORPORATION-BY-REFERENCE OF COMPUTER PROGRAM APPENDIX

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

STATEMENT REGARDING FEDERALLY SPONSORED RESEARCH OR DEVELOPMENT

This invention was made with government support under W31P4Q-12-1-0001 awarded by the Defense Advanced Research Projects Agency (DARPA). The government has certain rights in the invention.

BACKGROUND

1. Technical Field

The technology of this disclosure pertains generally to ultrasonic imaging, and more particularly to a Micro-machined Ultrasonic Transducer (MUT).

2. Background Discussion

The increasing market for mobile health indicates the growing consumer interest in low-cost and easy-to-use solutions for monitoring personal health. Weight, body-fat percentage and blood pressure are several critical indexes relating to a variety of chronic disease.

A weight scale integrated with impedance measuring devices provide a coarse full-body measurement on both weight and body-fat percentage, but are susceptible to multiple error sources, including humidity. There is also a lack of fitness usage devices capable of monitoring local muscle building effectiveness. Currently available blood pressure gauge (sphygmomanometer) devices are difficult to use without calibration and proficiency training.

A combination of these devices (weight, body-fat percentage and blood pressure) using currently available technology would clearly be excessively bulky for a portable device, and thus do not represent a workable solution for personal-health monitoring.

Alternatively, ultrasonic imaging which is now widely used in the medical field, provides accurate and local body-index measuring, including local body-fat assessment by measuring real thickness of body-fat and blood-pressure measuring by Doppler imaging on blood flow speed. The accuracy and local-body part measuring using ultrasonics overcomes many problems of traditional devices, while the size, complexity and huge power consumption of these devices remains an issue. The current problems preventing further miniaturize and integration of ultrasonic imaging include: (a) large and expensive ultrasonic transducer elements; (b) high-voltage requirements for driving the transducers; (c) requirements for multiple power supplies; and (d) lack of efficient level-shifting schemes from low voltage to high voltage.

Accordingly, a need exists for ultrasonic imaging which overcomes these shortcomings. The disclosed apparatus overcomes these shortcomings and provides additional benefits.

BRIEF SUMMARY

A miniature ultrasonic transmitter/receiver system is disclosed that may be implemented, such as using a CMOS ASIC and micro-machined ultrasonic transducers (MUTs). Applications for the system include measuring fat and muscle thickness at a particular human body part for healthcare purposes and muscle-training monitoring. In addition, the system has the capability of measuring blood-flow and blood-pressure. The disclosed apparatus can also provide for ultrasonic imaging of various physiological structures. Due to the small size and single low-voltage power supply of the system, this technology can also be integrated into portable devices for mobile health care. It should be appreciated that the device operates on principles of ultrasonic imaging, so it may be referred to as an ultrasonic imaging system even when not used for outputting images, that is to say when it is outputting information in other forms (e.g., blood pressure, blood flow, fat measure, muscle measure, etc.).

The technology of this disclosure also relates to the use of DC-DC converter and MEMS/CMOS technology to perform ultrasonic imaging with a single supply. In the current embodiment, a charge-pump is integrated within a CMOS ASIC to handle the high-voltage requirement. High fill-factor MUTs with flexural modes are used for providing significant levels of acoustic impedance matching and easy fabrication compatibility (e.g., CMOS-compatible fabrication), such as for a two-dimensional (2D) array. A spatial array of MUTs is used with delay-control electronics to enable both transmitting/receiving beam-forming and beam-steering.

In order to create a portable device suitable for taking physiological measurements for personal health care, it is desirable to build a sensor system having a size of less than approximately one cubic centimeter (<1 cm$^3$) size and having a power consumption per measurement at about µJ levels toward accommodating use with a variety of portable devices.

By way of example and not limitation, the disclosed technology can be utilized in the following situations, among others.

1. Body-fat and muscle thickness measurement, including: (a) a non-invasive way to determine body-fat percentage by accurate measurement on both muscle and fat thickness; (b) a local body-part measurement could be performed instead of full-body assessment; (c) to provide constant (continuous) monitoring of a users' body-fat; (d) to determine the effect of exercising by measuring the actual body muscle thickness.

2. Blood pressure measurement, including: (a) using Doppler imaging techniques to determine blood-flow speed; (b) determining blood-vessel information, such as wall diameter and thickness, based on information obtained using pulse-echo ultrasonic imaging; (c) determining blood pressure derived by the two measurements above.

3. Local body-part ultrasonic imaging, including: (a) performing ultrasonic imaging on local body part for preventive investigations; (b) performing ultrasonic imaging on eye lens for myopia diagnosis; and (c) performing ultrasonic imaging on skin for determining skin-aging and facilitating cosmetic supervision.

Further aspects of the technology described herein will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWING(S)

The technology described herein will be more fully understood by reference to the following drawings which are for illustrative purposes only:

DETAILED DESCRIPTION

The technology described herein is a miniature ultrasonic imager. In one embodiment, the imager is configured to perform in-vivo imaging of regions on a user's body. In at least one preferred embodiment, the imager can be programmed to perform 1D imaging (A-Scan), 2D imaging (B-Scan), 3D imaging (C-Scan) and Doppler imaging.

Figure 1:
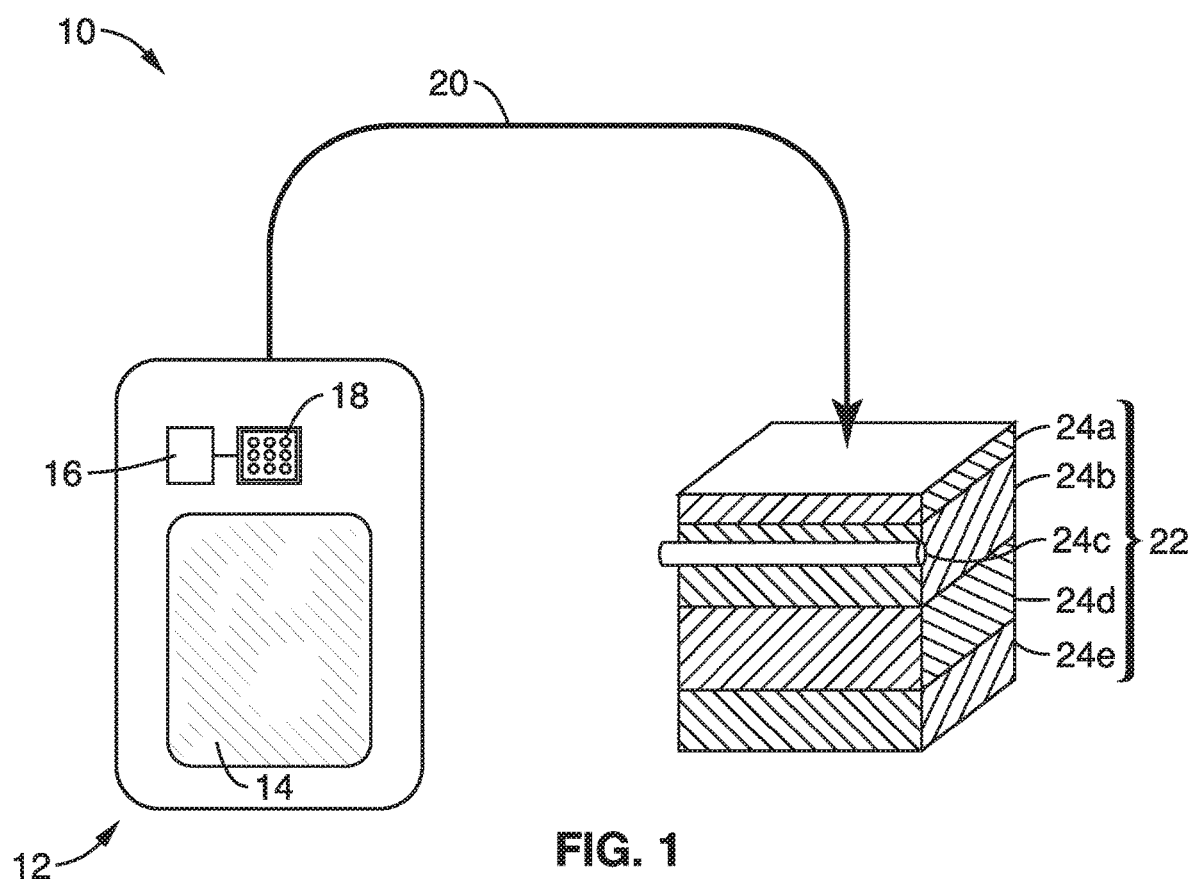
FIG. 1 is a block diagram of an ultrasound sensor according to an embodiment of the present disclosure shown mounted on a computing device and directed at a skin surface target.

FIG. 1 illustrates an embodiment 10 of an ultrasonic imaging system. By way of example, a portable device 12, having display 14 (e.g., touch screen) is shown with an ultrasonic imager circuit to emit ultrasonic waves. Display screen 14 may also provide touch input for user I/O, such as for supporting a graphical user interface (GUI), or other user interfacing. The ultrasonic imager comprises an ultrasonic imaging sensor array 18 coupled to a processor 16, such as within an application specific integrated circuit (ASIC), which may be coupled to (mounted upon) the portable electronic device and/or integrated within it.

During operation, the user contacts the imager 18, to a local body part area 22, upon which ultrasonic wave are emitted (transmitted) into that area of the patient's body. Arrow 20 merely represents the movement of imager 18 to achieve contact with body area 22. The imager collects (receives) the reflected sound wave signal and the processor processes the imager output data into the desired information for providing health information and displaying the result on screen. It will be noted that the information may be displayed in any desired form, from numerical statistics, graphs, plots, and so forth, and/or include images collected from the imager.

In the figure, the ultrasonic imager 18 is configured for contacting the target 22, herein depicted as the skin of patient, with upper skin surface 24a, subcutaneous fat 24b, blood vessel 24c, muscle 24d, and bone 24e. It will be appreciated that the ultrasonic imager may extend from the housing of the portable device in any desired manner (e.g., protrusion, on a cable, wireless interface, etc.) so as to allow making contact with the target.

A small MUT pitch (spacing between electrodes) is preferable for providing a high fill factor which is important for the array to reduce grating lobe. It will be noted that grating lobes, and side lobes, are two closely related phenomena that are caused by sound energy spreading out from the transducer at angles other than the primary path. It will be appreciated that electrostatics and piezoelectricity principles are relied upon for energy conversion between electrical and mechanical domains in ultrasonic transducers. It should also be appreciated that embodiments of the present disclosure may be configured using Piezoelectric MUTs (PMUTs) and capacitive MUTs (CMUTs), which have thin membrane and work in flexural vibration modes. Both CMUTs and PMUTs can be fabricated using currently available batch fabrication techniques for semiconductors. It should also be appreciated that MUTs and complementary metal-oxide semiconductors (CMOS) application specific integrated circuits (ASICs) can be integrated using either wafer bonding or wire bonding technologies.

Figure 2:
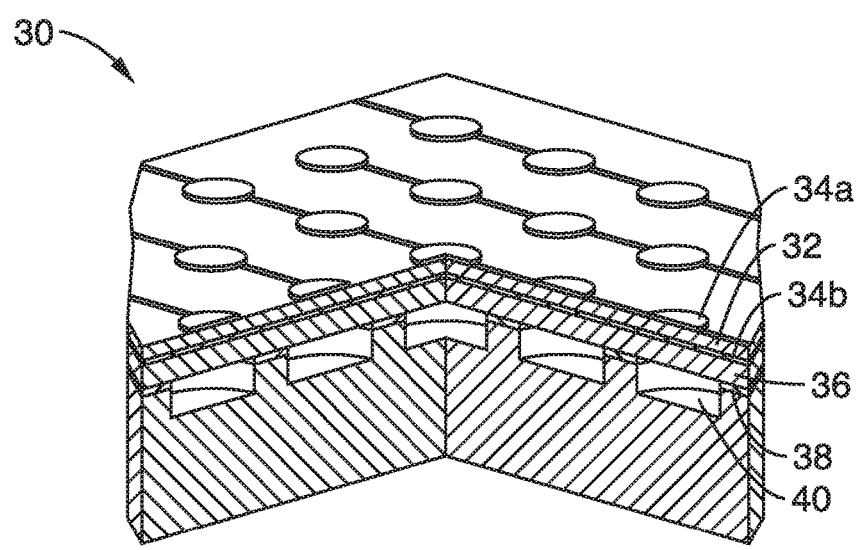
FIG. 2 is a cutaway view of a PMUT array based on cavity SOI wafers according to an embodiment of the present disclosure.
Figure 3A:
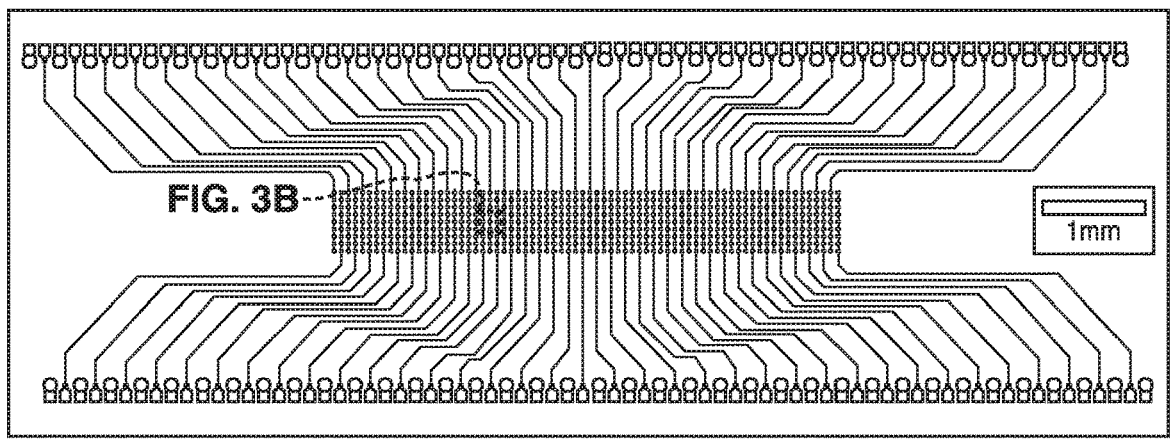
FIG. 3A and FIG. 3B are views of a PMUT array according to an embodiment of the present disclosure, with FIG. 3B depicting an electrode area from FIG. 3A as magnified.
Figure 3B:
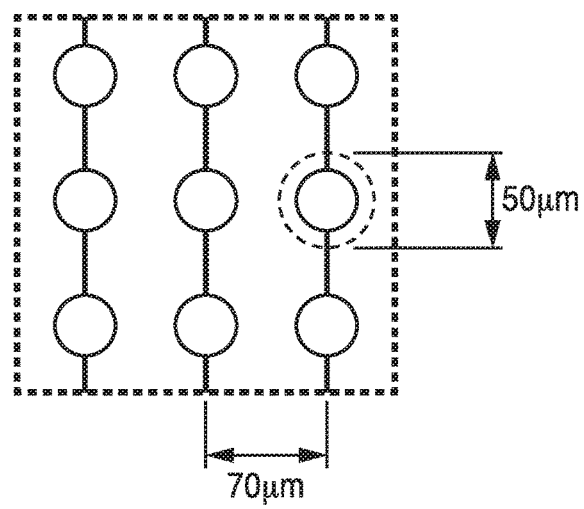
Figure 4:
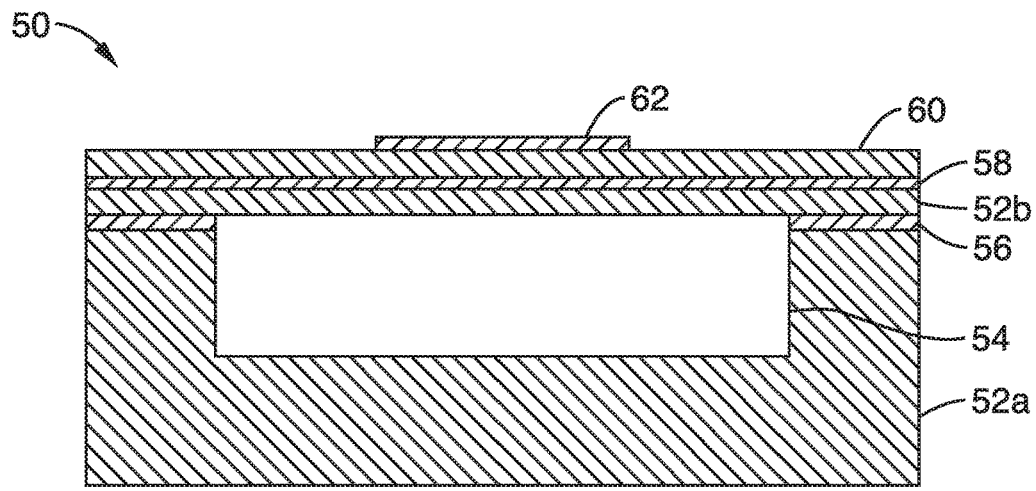
FIG. 4 is a cross-section view of a single transducer of a PMUT array according to an embodiment of the present disclosure, showing the top electrode disposed over a substrate having a cavity.

FIG. 2 through FIG. 4 illustrate a PMUT embodiment, which utilizes a piezoelectric material to achieve energy conversion between electrical and mechanical domains. The PMUT operates as both a transmitter and receiver for generating and sensing acoustic pressure. As a transmitter, with voltage load on electrodes, the electric field between the top electrode (TE) and the bottom electrode (BE) generates a transverse stress in the AlN piezoelectric layer due to the inverse piezoelectric effect. The generated stress causes a bending moment which forces the membrane to deflect out of plane. The applied opposing voltages generate different signs of stress inside the piezoelectric layer, and therefore moves the membrane up and down, and launches an acoustic pressure wave into the environment. As a receiver, an incident pressure wave deflecting the PMUT membrane creates transverse stress inside the piezoelectric layer. The stress results in a charge between the electrodes due to direct piezoelectric effect. The generated charge and therefore incident pressure can be obtained through measuring the voltage between electrodes.

In FIG. 2 a cutaway of a PMUT embodiment 30 is shown having a piezoelectric layer 32, over which is disposed a top electrode pattern 34a. Beneath the piezoelectric layer 32 there is shown a bottom electrode 34b, and a device semiconductor 36 (e.g., Si depicted by way of example), followed by dielectric regions 38 (e.g., $SiO_2$), and cavities 40.

FIG. 3A and FIG. 3B show a trace pattern of a PMUT ASIC as seen in FIG. 3A, with electrode areas magnified in FIG. 3B, shown with example electrode area of 50 µm, and a pitch (spacing between electrodes) of 70 µm.

FIG. 4 illustrates an embodiment 50 of a PMUT showing a single electrode 62 over a cavity region 54. A material substrate 52a (e.g., Si) is shown into which a cavity 54 is formed, typically by a subtractive process (i.e., etching), over which is deposited a dielectric layer 56 (e.g., $SiO_2$), above which is another material layer 52b (e.g., Si), bottom electrode 58, piezoelectric layer 60, upon which electrode 62 is disposed.

Figure 5:
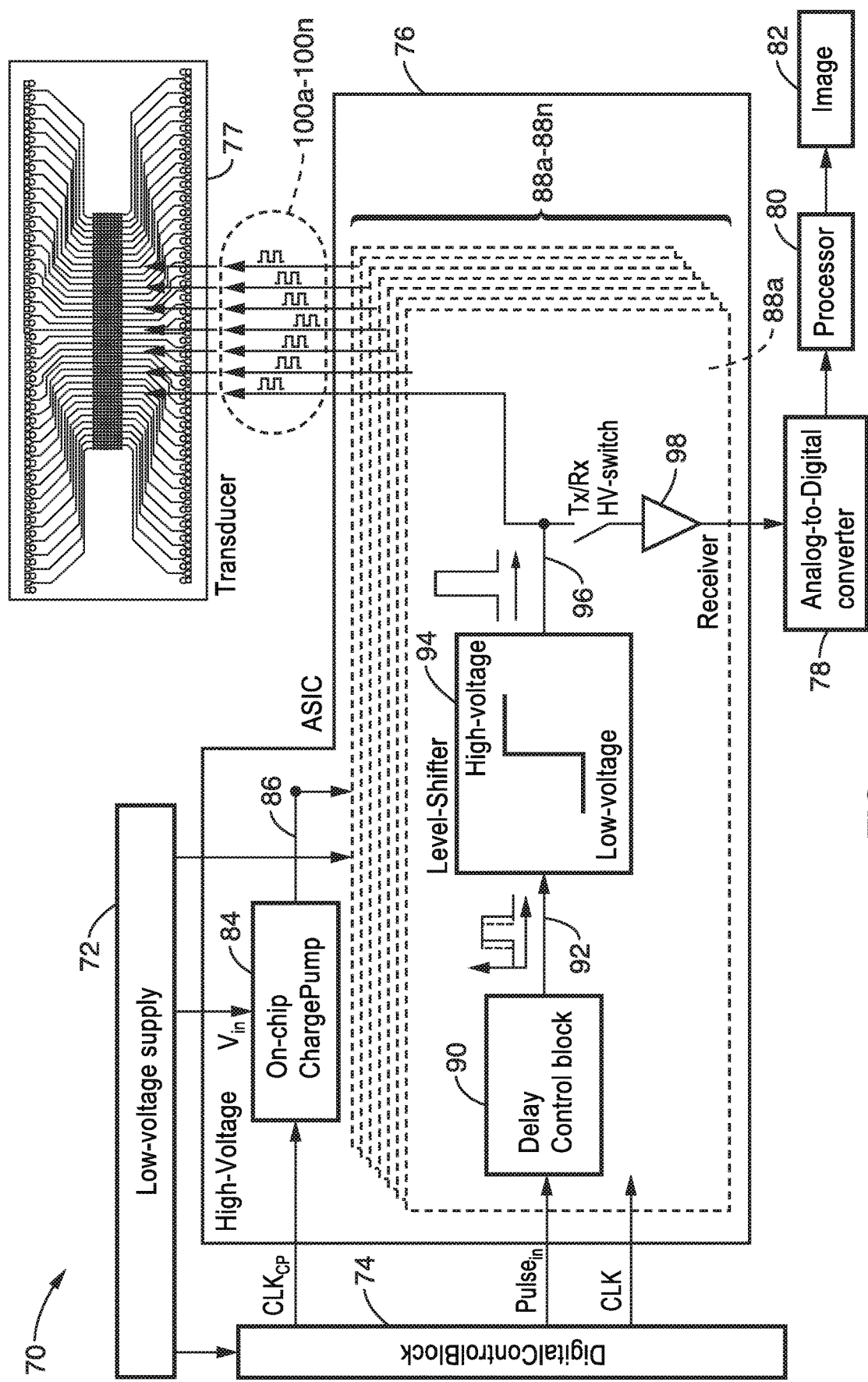
FIG. 5 is a schematic of an ultrasonic imaging sensor according to an embodiment of the present disclosure.

FIG. 5 illustrates an an ultrasonic sensor 70 comprising a low voltage supply 72 and digital control block 74 supplying power and control to an ASIC array 76, shown coupled to a PMUT transducer array 77. Output from ASIC 76 is shown being received at an analog-to-digital converter (ADC) 78 before receipt by at least one processing element 80 which processes the ultrasonic data to generate image data, which can be processed as an image output 82 directed to a display. It should also be recognized that the image data can be processed to extract salient features, whereby results can be output for display, plotting, analysis and so forth.

Within the ASIC are several identical channels 88a through 88n, although only the elements on channel 88a can be seen in the figure. A high-voltage charge pump 84 outputs a high voltage 86 which is applied to the high-voltage level-shifter as required throughout transmitting operation. When transmitting, an input low-voltage pulse is directed into each channel and delayed by the amount determined by delay control unit 90. The delayed signal 92, then enters a high-voltage level shifter 94 which outputs a level-shifted output 96 to drive the sensor array seen as outputs 100a through 100n directed at PMUT 77. An optional buffer can be inserted between sensors and level-shifter for more efficient driving.

FIG. 6A through FIG. 7D illustrate a comparison between level-shifter embodiments by way of example and not limitation.

Figure 6A:
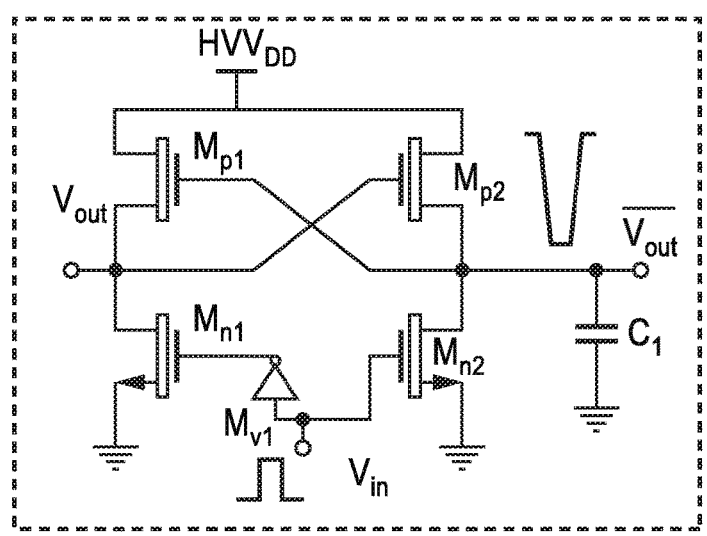
FIG. 6A through FIG. 6C is a static level-shifter design for high-voltage driving, and which exhibits problematic large crowbar-currents.
Figure 6B:
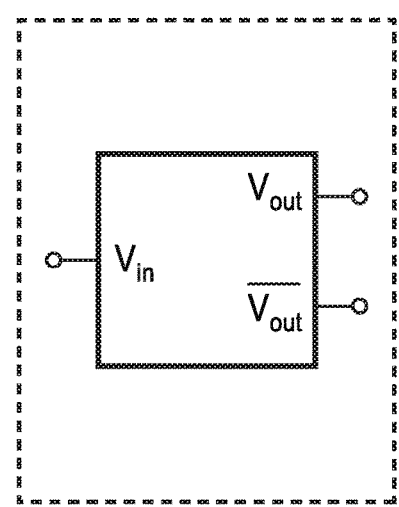
Figure 6C:
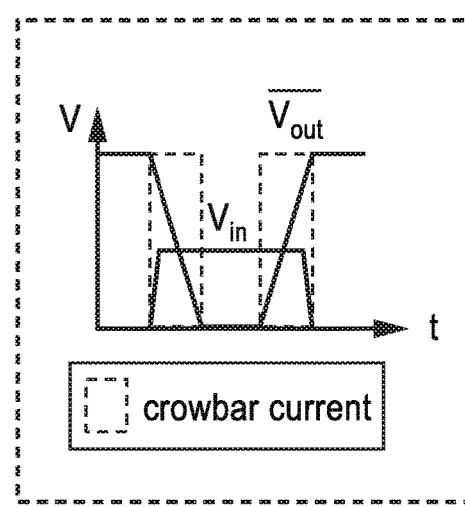

It should be appreciated that the conventional latch-based solution of FIG. 6A through FIG. 6C exceeds the current capabilities of on-chip charge-pumps owing to the large crowbar current flowing during the switching transient. The transistors shown are high voltage transistors symbolized as an enlarged (box) S-D junction. In FIG. 6A a latch form level-shifter 110 is seen with power $HVV_{DD}$ and a pulse voltage input V. Complementary transistors $M_{p1}$, $M_{n1}$ are seen cross coupled with complementary transistors $M_{p2}$, $M_{n2}$, the circuit driving outputs $V_{out}$ and $V_{out}'$, with at least one coupled to a capacitor $C_1$. A schematic representation is shown 112 in FIG. 6B. A voltage plot is seen in FIG. 6C depicting the switching of $V_{out}$ in response to $V_{in}$, with areas marked in gray showing the times in which large crossbar currents are drawn.

The disclosed level-shifter shown in FIG. 7A through FIG. 7D adds switches to prevent a conducting path from the supply to ground. The switches are opened before the low-to-high transition of positive input signal and closed after the output has settled. This effectively removes the pull-up transistor from the output during the transition, thus enabling the use of a small NMOS pull-down transistor with low input capacitance and permitting high-speed operation.

Figure 7A:
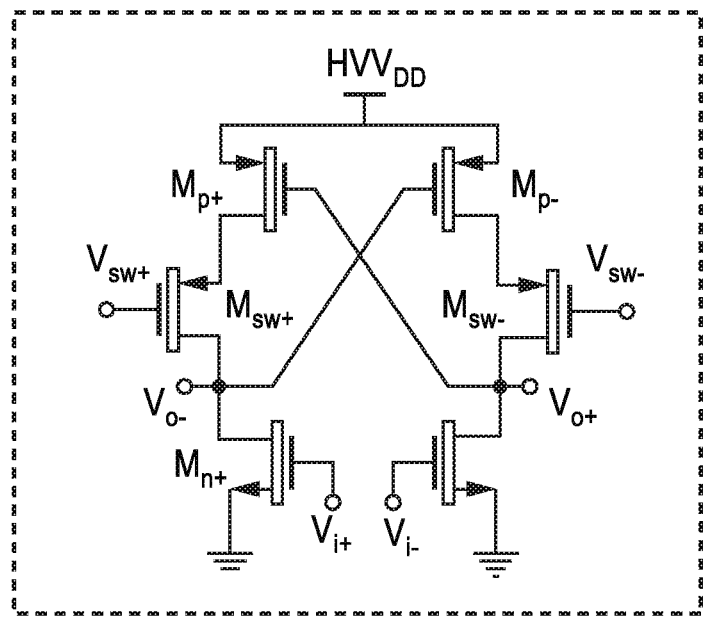
FIG. 7A through FIG. 7D is a crowbar-current-free dynamic level-shifter design for high-voltage driving according to an embodiment of the present disclosure.

In FIG. 7A is illustrated a level shifter embodiment 114 seen with power $HVV_{DD}$ and a complementary pulse voltage input $V_{i+}$, $V_{i-}$. Complementary transistors $M_{p+}$, $M_{n+}$ are seen cross coupled with complementary transistors $M_{p-}$, $M_{n-}$, the circuit driving outputs $V_{o+}$ and $V_{o-}$. Two switches $M_{sw+}$ and $M_{sw-}$ are high voltage transistors, each coupled between the upper and lower complementary pairs.

Figure 7B:
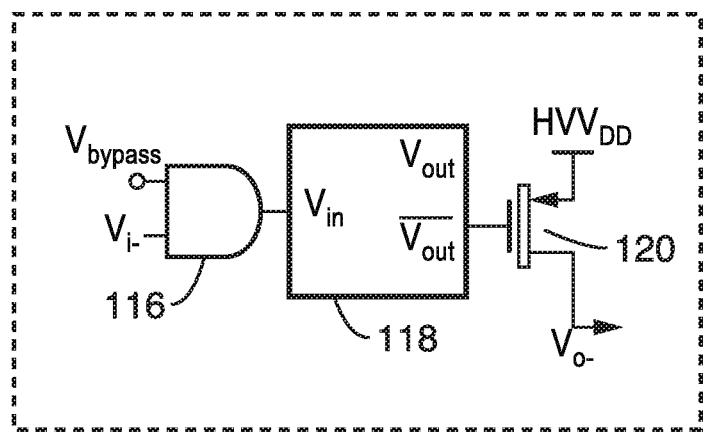

In FIG. 7B is seen a bypass switch for static operations. An AND gate 116 is seen with inputs $V_{bypass}$ and $V_i$, which outputs to a level translator 118, outputting $V_{out}'$ that drives a high-voltage transistor 120 for outputting $V_{o-}$.

Figure 7C:
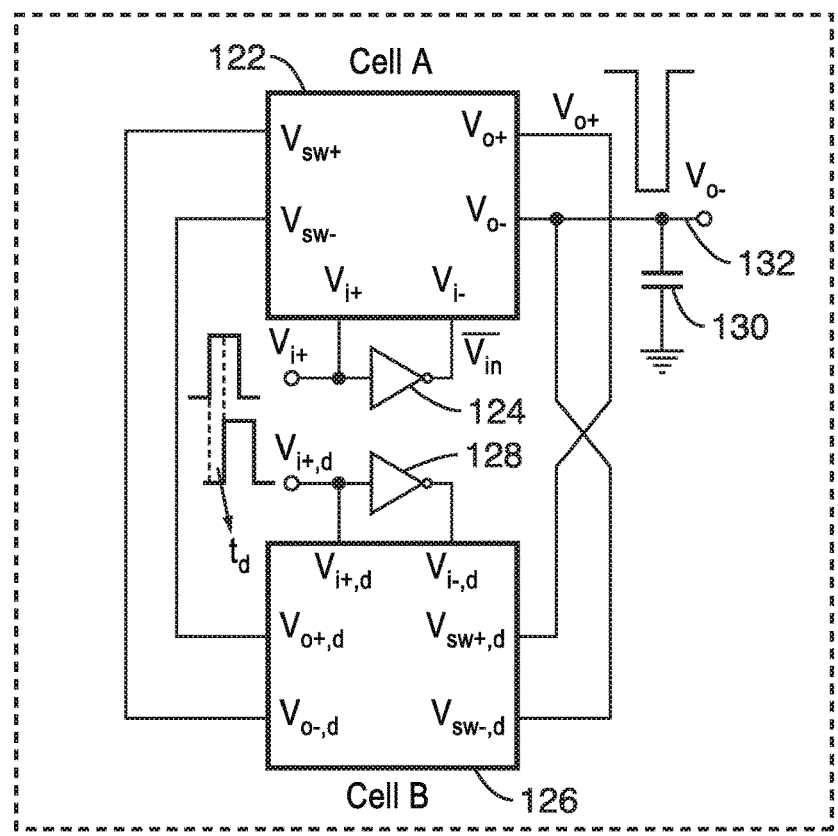
Figure 7D:
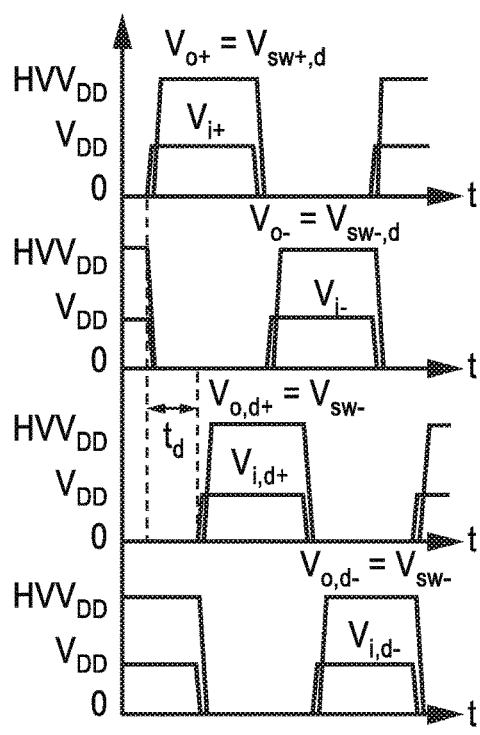

Referring to FIG. 7A, it will be noted that the high voltage transistors require high-voltage controls themselves. This requirement is met in at least one embodiment with an auxiliary level-shifter, as seen in FIG. 7C. The primary and auxiliary shifters, cell A 122 with inverter 124, and cell B 126 with inverter 128, are cross-coupled to generate output $V_o$_132 to drive the load capacitor ($C_L$) 130. It will be noted that all required control signals are generated, as indicated in the timing diagram seed in FIG. 7D. The input to Cell B is delayed by a certain amount of delay (seen as delay interval $t_d$) with respect to the input control of Cell A. In the four transitions shown in FIG. 7D it can be seen that there are no regions in which crowbar currents arise.

Figure 8A:
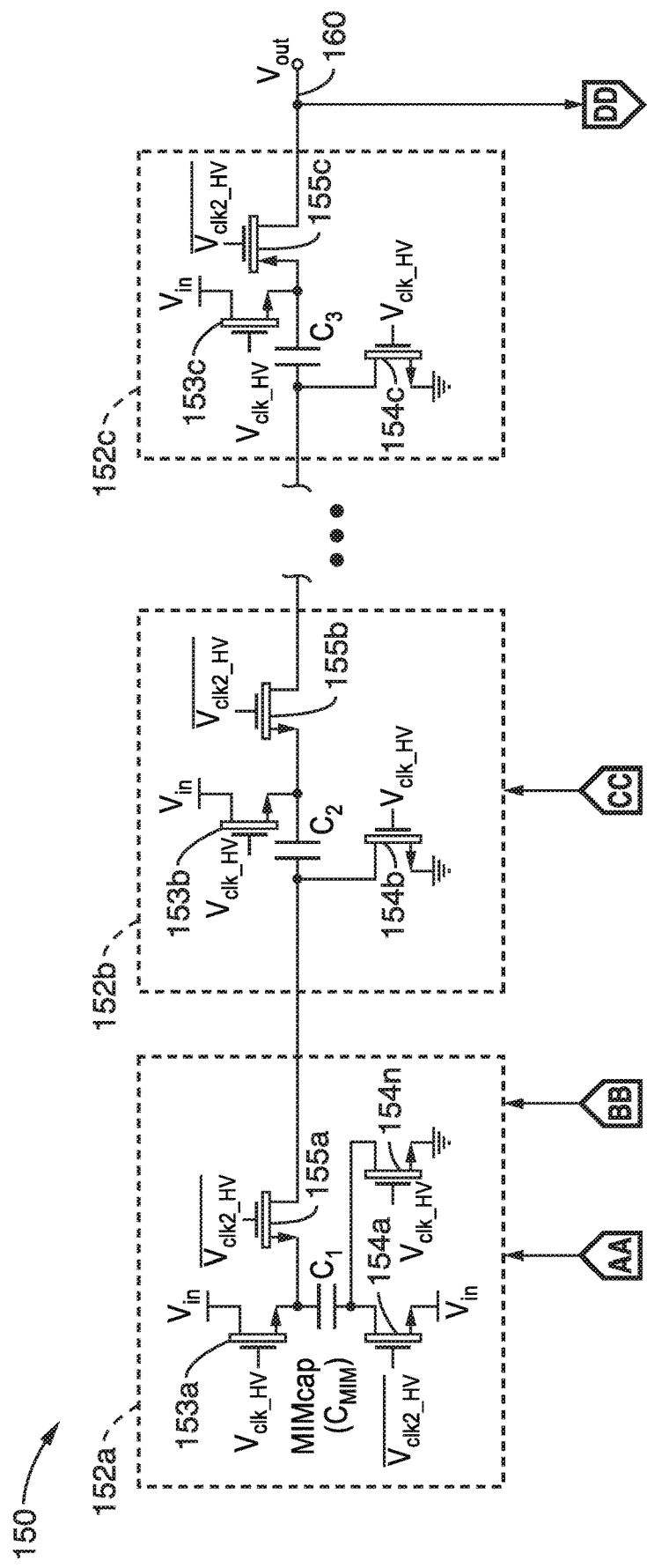
FIG. 8A and FIG. 8B is a schematic of a high voltage charge pump according to an embodiment of the present disclosure.
Figure 8B:
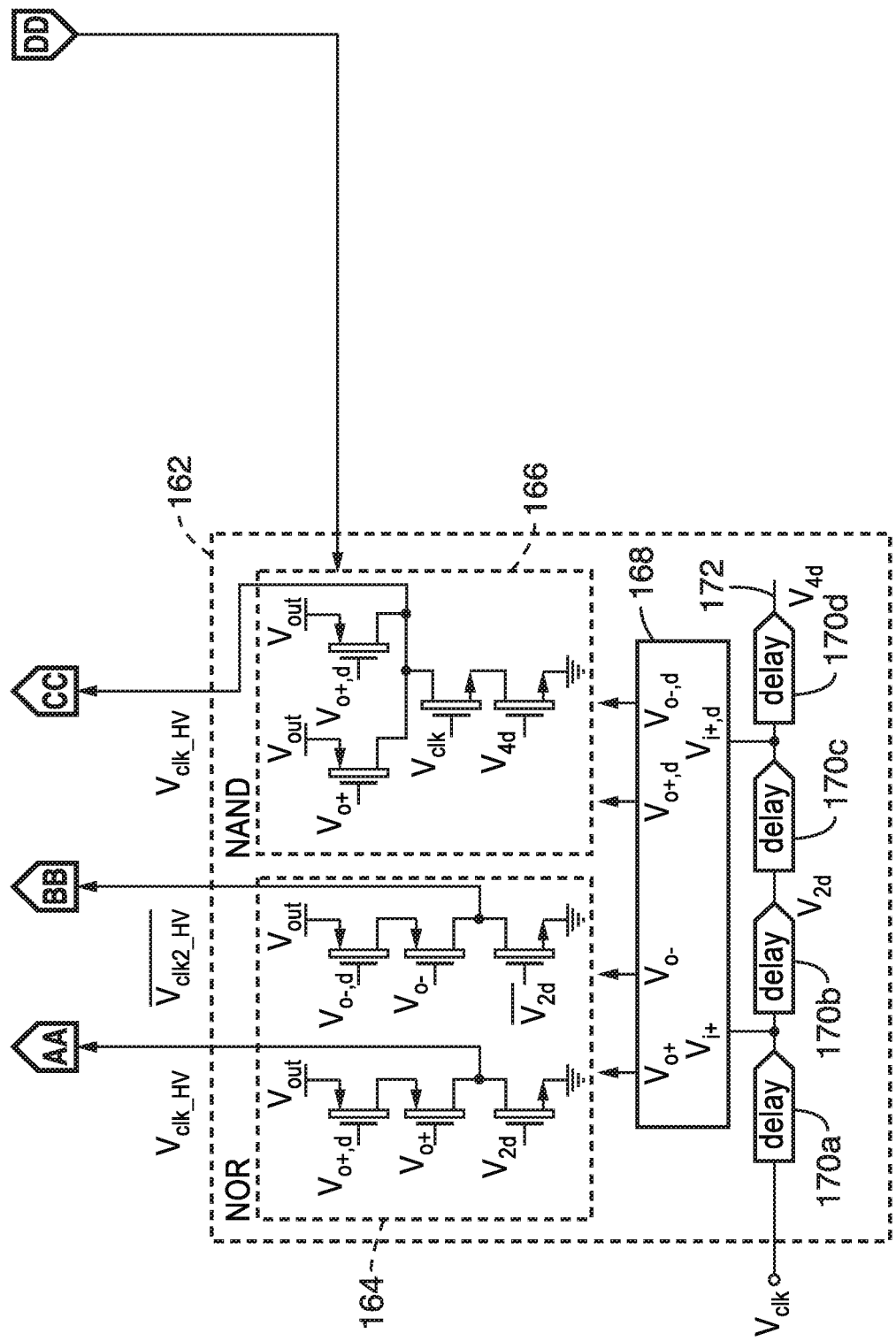

FIG. 8A and FIG. 8B illustrate one possible embodiment 150 of a series-parallel charge-pump 152a to 152c, driven by a non-overlapping clock generator 162. The charge pump is exemplified in three stages with cell 1 seen as 152a, cells 2 to 4 seen in 152b, and cells 5 to 7 seen in 152c, which together generate $V_{out}$ 160. These stages comprise high voltage switches 153a to 153c, 154a to 154c, 155a to 155c, flying capacitors $C_2$-$C_3$, storage capacitor $C_1$ and clock generator 162. Clock generator 162 is shown with a high voltage NOR stage 164, and a high voltage NAND stage 166, driven from translated voltages 168 from delays 170a to 170d (using signals $V_{2d}$ and $V_{4d}$) from $V_{clk}$. The clock generator produces non-overlapping high-voltage clocks to operate the charge pump. In at least one embodiment, the level-shifter design previously described was also used in the clock generator to minimize operating power.

One will appreciate that the PMUT shown in FIG. 2, is readily modified as a CMUT, by removing/replacing the piezoelectric layer 32, and registering capacitive changes as the distance between the top and bottom electrode changes. In a CMUT a piezoelectric material is not required for performing energy conversion between electrical and mechanical domains, as these are created in response to capacitive effects. Capacitive micromachined ultrasonic transducer (CMUT) arrays can similarly provide ultrasonic imaging with relatively wide bandwidth. CMUT arrays are composed of many micromachined thin membranes that can be actuated and detected capacitively. Due to a CMUT being a subset of the PMUT in FIG. 2, a separate figure for CMUTs was not shown.

The operation of the ultrasonic imaging system (e.g., as in FIG. 5) is described below. A measurement cycle begins when the transmitter generates a high-voltage transmit pulse with a determined (selected) delay controlled by delay control unit for driving the ultrasonic transducer elements. The generated acoustic pulses propagate into the body and are reflected by various boundaries where the two kinds of material have different acoustic impedances. The reflected acoustic pulses travel back to one or more transducer elements. The amplitude and phase of the reflected pulses can be used to obtain material property and depth of the boundary. Also during transmission the switch is opened to isolate the receiver from the high-voltage transmitting signal. After the transmitting cycle is complete, the switch is closed and the receiver begins receiving. The received echo arrives at the transducer after a delay according to the range to the reflecting surface. The receiver electronics amplify the signal and analog to digital converter (ADC) converts the analog received signal to a digital form and filters the signal further. Finally, the processor reconstructs the signal and displays the desired image.

The ultrasonic imaging system described in the presented technology can be readily implemented in an electronic system, integrated within existing portable electronic systems, or implemented as add-on hardware controlled by an application program running on a smart device, or other computer-processor based platform. It should also be appreciated that ultrasonic image processors are preferably implemented to include one or more computer processor devices (e.g., CPU, microprocessor, microcontroller, computer enabled ASIC, etc.) and associated memory storing instructions (e.g., RAM, DRAM, NVRAM, FLASH, computer readable media, etc.) whereby programming (instructions) stored in the memory are executed on the processor to perform the steps of the various process methods described herein. The presented technology is non-limiting with regard to memory and computer-readable media, insofar as these are non-transitory, and thus not constituting a transitory electronic signal.

Embodiments of the present technology may be described herein with reference to flowchart illustrations of methods and systems according to embodiments of the technology, and/or procedures, algorithms, steps, operations, formulae, or other computational depictions, which may also be implemented as computer program products. In this regard, each block or step of a flowchart, and combinations of blocks (and/or steps) in a flowchart, as well as any procedure, algorithm, step, operation, formula, or computational depiction can be implemented by various means, such as hardware, firmware, and/or software including one or more computer program instructions embodied in computer-readable program code. As will be appreciated, any such computer program instructions may be executed by one or more computer processors, including without limitation a general purpose computer or special purpose computer, or other programmable processing apparatus to produce a machine, such that the computer program instructions which execute on the computer processor(s) or other programmable processing apparatus create means for implementing the function(s) specified.

Accordingly, blocks of the flowcharts, and procedures, algorithms, steps, operations, formulae, or computational depictions described herein support combinations of means for performing the specified function(s), combinations of steps for performing the specified function(s), and computer program instructions, such as embodied in computer-readable program code logic means, for performing the specified function(s). It will also be understood that each block of the flowchart illustrations, as well as any procedures, algorithms, steps, operations, formulae, or computational depictions and combinations thereof described herein, can be implemented by special purpose hardware-based computer systems which perform the specified function(s) or step(s), or combinations of special purpose hardware and computer-readable program code.

Furthermore, these computer program instructions, such as embodied in computer-readable program code, may also be stored in one or more computer-readable memory or memory devices that can direct a computer processor or other programmable processing apparatus to function in a particular manner, such that the instructions stored in the computer-readable memory or memory devices produce an article of manufacture including instruction means which implement the function specified in the block(s) of the flowchart(s). The computer program instructions may also be executed by a computer processor or other programmable processing apparatus to cause a series of operational steps to be performed on the computer processor or other programmable processing apparatus to produce a computer-implemented process such that the instructions which execute on the computer processor or other programmable processing apparatus provide steps for implementing the functions specified in the block(s) of the flowchart(s), procedure (s) algorithm(s), step(s), operation(s), formula(e), or computational depiction(s).

It will further be appreciated that the terms "programming" or "program executable" as used herein refer to one or more instructions that can be executed by one or more computer processors to perform one or more functions as described herein. The instructions can be embodied in software, in firmware, or in a combination of software and firmware. The instructions can be stored local to the device in non-transitory media, or can be stored remotely such as on a server, or all or a portion of the instructions can be stored locally and remotely. Instructions stored remotely can be downloaded (pushed) to the device by user initiation, or automatically based on one or more factors.

It will further be appreciated that as used herein, that the terms processor, computer processor, central processing unit (CPU), and computer are used synonymously to denote a device capable of executing the instructions and communicating with input/output interfaces and/or peripheral devices, and that the terms processor, computer processor, CPU, and computer are intended to encompass single or multiple devices, single core and multicore devices, and variations thereof.

From the description herein, it will be appreciated that that the present disclosure encompasses multiple embodiments which include, but are not limited to, the following:

1. An ultrasonic transmitter/receiver apparatus, comprising: (a) an ultrasonic imaging array comprising a plurality of piezoelectric micro-machined ultrasonic transducers (PMUTs), each comprising: (a)(i) a first electrode layer comprising a plurality of electrodes configured in an array; (a)(ii) a piezoelectric layer adjacent the first electrode layer; and (a)(iii) a second electrode layer adjacent the piezoelectric layer; (a)(iv) wherein each said PMUT is configured with a transmitting mode for generating acoustic pressure, and a receiving mode for sensing acoustic pressure; and (b) a control circuit structure, coupled to the ultrasonic imaging array, with said control circuit configured for controlling said generation of acoustic pressure, controlling receiving information on acoustic pressure, and processing configured for analyzing said acoustic pressure information to generate physiological measurements.

2. The apparatus of any preceding embodiment, wherein said physiological measurements are selected from the group of physiological measurements consisting of: body fat thickness measurement, muscle thickness measurement, blood-flow measurement, blood-pressure measurement, and ultrasonic imaging.

3. The apparatus of any preceding embodiment, wherein in the transmitting mode, a voltage load applied to the electrode layers creates an electric field between the first electrode and the second electrode that generates a transverse stress in the piezoelectric layer due to an inverse piezoelectric effect, wherein the generated stress causes a bending moment in the PMUT structure that causes deflection out of plane, and wherein applied different signs of voltage generates different signs of stress inside piezoelectric layer that in turn causes an oscillating motion that generates an acoustic pressure wave.

4. The apparatus of any preceding embodiment, wherein in the receiving mode, an incident pressure wave deflecting the PMUT structure creates transverse stress inside the piezoelectric layer, wherein the stress results in a charge between the electrode layers due to direct piezoelectric effect, and wherein the generated charge and therefore incident pressure can be obtained through measuring voltage between electrodes.

5. The apparatus of any preceding embodiment, wherein the control circuit structure comprises: (a) an application specific integrated circuit (ASIC) having a plurality of channels each with a delay control unit; (b) a high-voltage level-shifter; (c) a high-voltage charge pump configured to supply high-voltage to the high-voltage level-shifter for the transmitting mode, wherein when transmitting, an input low-voltage signal directed into each channel is delayed by an amount determined by delay control unit, and wherein the delayed signal is then level-shifted by high-voltage level shifters to drive the electrode array; and (d) a receive/transmit switch configured to isolate the high voltage used in the transmitting mode from components used during the receiving mode.

6. The apparatus of any preceding embodiment, wherein said array into which said plurality of electrodes are configured comprises a two dimensional (2D) array.

7. The apparatus of any preceding embodiment, wherein said apparatus comprises a spatial array of PMUTs which are utilized with delay-control circuits for enabling transmitter beam forming, or receiver beam-steering, or a combination of transmitter beam forming and receiver beam-steering.

8. The apparatus of any preceding embodiment, wherein said ultrasonic transmitter/receiver apparatus is configured for use with, integration with, or integration within, a portable electronic device.

9. The apparatus of any preceding embodiment, wherein said apparatus is configured for measuring fat and muscle thickness at a particular human body part.

10. The apparatus of any preceding embodiment, wherein said apparatus is configured for measuring blood-flow and blood-pressure.

11. An ultrasonic transmitter/receiver apparatus, comprising: (a) an ultrasonic imaging array comprising a plurality of micro-machined ultrasonic transducers (MUTs), each comprising: (a)(i) a first electrode layer comprising a plurality of electrodes configured in an array; (a)(ii) a dielectric layer adjacent the first electrode layer; and (a)(iii) a second electrode layer adjacent the dielectric layer; (a)(iv) wherein each said MUT is configured with a transmitting mode for generating acoustic pressure, and a receiving mode for sensing acoustic pressure; and (b) a control circuit structure, coupled to the ultrasonic imaging array, with said control circuit is configured for controlling said generation of acoustic pressure, controlling receiving information on acoustic pressure, and processing configured for analyzing said acoustic pressure information to generate physiological measurements.

12. The apparatus of any preceding embodiment, wherein said MUTs comprise either piezoelectric micro-machined ultrasonic transducers (PMUTs), or capacitive micro-machined ultrasonic transducers (CMUTs).

13. The apparatus of any preceding embodiment, wherein said physiological measurements are selected from the group of physiological measurements consisting of: body fat thickness measurement, muscle thickness measurement, blood-flow measurement, blood-pressure measurement, and ultrasonic imaging.

14. The apparatus of any preceding embodiment, wherein the control circuit structure comprises: (a) an application specific integrated circuit (ASIC) having a plurality of channels each with a delay control unit; (b) a high-voltage level-shifter; (c) a high-voltage charge pump configured to supply high-voltage to the high-voltage level-shifter for the transmitting mode, wherein when transmitting, an input low-voltage signal directed into each channel is delayed by an amount determined by delay control unit, and wherein the delayed signal is then level-shifted by high-voltage level shifters to drive the electrode array; and (d) a receive/transmit switch configured to isolate the high voltage used in the transmitting mode from components used during the receiving mode.

15. The apparatus of any preceding embodiment, wherein said array into which said plurality of electrodes are configured comprises a two dimensional (2D) array.

16. The apparatus of any preceding embodiment, wherein said apparatus comprises a spatial array of MUTs which are utilized with delay-control circuits for enabling transmitter beam forming, or receiver beam-steering, or a combination of transmitter beam forming and receiver beam-steering.

17. The apparatus of any preceding embodiment, wherein said ultrasonic transmitter/receiver apparatus is configured for use with, integration with, or integration within, a portable electronic device.

18. The apparatus of any preceding embodiment, wherein said apparatus is configured for measuring fat and muscle thickness at a particular human body part.

19. The apparatus of any preceding embodiment, wherein said apparatus is configured for measuring blood-flow and blood-pressure.

20. A method of performing ultrasonic imaging, comprising: (a) commencing a measurement cycle by generating high-voltage transmit pulses on a plurality of micro-machined ultrasonic transducers (MUTs); (b) wherein each said transmit pulse is generated with a selected delay for driving the ultrasonic transducer elements so that generated acoustic pulses propagate into a portion of a users body and are reflected by various boundaries therein in which material layers have different acoustic impedances; (c) switching to a receiving mode in which a receiver is isolated from the high-voltage transmitting signal; (d) receiving reflected acoustic pulses back to said plurality of micro-machined ultrasonic transducers (MUTs); (e) analyzing amplitude and phase of the received reflected acoustic pulses to determine material properties and depth of boundaries; (f) wherein the reflected acoustic pulses are received at the MUTs after a delay according to the range to the reflecting surface; and (g) converting the received pulses into a digital form and reconstructing ultrasonic signals into an ultrasonic image.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

What is claimed is:

1. An ultrasonic transmitter/receiver apparatus, comprising:
   (a) an ultrasonic imaging array comprising a plurality of piezoelectric micro-machined ultrasonic transducers (PMUTs), each comprising:
      (i) a first electrode layer comprising a plurality of electrodes configured in an array;
      (ii) a piezoelectric layer adjacent the first electrode layer; and
      (iii) a second electrode layer adjacent the piezoelectric layer;
      (iv) wherein each said PMUT is configured with a transmitting mode for generating acoustic pressure, and a receiving mode for sensing acoustic pressure;
   (b) a control circuit structure, coupled to the ultrasonic imaging array, with said control circuit configured for controlling said generation of acoustic pressure, controlling receiving information on acoustic pressure, and processing configured for analyzing said acoustic pressure information to generate physiological measurements;
   (c) wherein said control circuit structure comprises an application specific circuit having a charge pump and an array of channel circuits each configured for interfacing with channels within said ultrasonic imaging array;
   (d) wherein each said channel circuit is configured to generate an output to a an analog-to-digital converter of a receiver whose output is directed to a computer processing element configured for processing ultrasonic data from said ultrasonic imaging array to generate image data to a display;
   (e) wherein each channel circuit comprises a high voltage level shifter, a delay control circuit, and a transmit/receive switch;
   (f) wherein each channel circuit is configured to receive a high voltage output from the charge pump which is applied to said high-voltage level-shifter in the channel circuit, said high-voltage level-shifter is configured for outputting a level-shifted output of sufficient voltage to drive channels in said ultrasonic imaging array;
   (g) wherein said delay control circuit is configured for receiving a low-voltage pulse input from said control circuit and delaying it by a determined amount in each channel circuit before an output is generated to drive said high voltage level shifter; and
   (h) wherein said transmit/receive switch is configured for isolating the receiver from high transmit voltages generated during transmission.

2. The apparatus of claim 1, wherein said physiological measurements are selected from the group of physiological measurements consisting of: body fat thickness measurement, muscle thickness measurement, blood-flow measurement, blood-pressure measurement, and ultrasonic imaging.

3. The apparatus of claim 1, wherein in the transmitting mode, a voltage load applied to the electrode layers creates an electric field between the first electrode and the second electrode that generates a transverse stress in the piezoelectric layer due to an inverse piezoelectric effect, wherein the generated stress causes a bending moment in the PMUT structure that causes deflection out of plane, and wherein applied different signs of voltage generates different signs of stress inside piezoelectric layer that in turn causes an oscillating motion that generates an acoustic pressure wave.

4. The apparatus of claim 1, wherein in the receiving mode, an incident pressure wave deflecting the PMUT structure creates transverse stress inside the piezoelectric layer, wherein the stress results in a charge between the electrode layers due to direct piezoelectric effect, and wherein the generated charge and therefore incident pressure can be obtained through measuring voltage between electrodes.

5. The apparatus of claim 1, wherein the application specific integrated circuit (ASIC) having a plurality of channels each with a delay control unit the high-voltage level-shifter and the charge pump configured to supply high-voltage to the high-voltage level-shifter for the transmitting mode, wherein when transmitting, an input low-voltage signal directed into each channel is delayed by an amount determined by delay control unit, and wherein the delayed signal is then level-shifted by high-voltage level shifters to drive the electrode array; and
   a receive/transmit switch configured to isolate the high voltage used in the transmitting mode from components used during the receiving mode.

6. The apparatus of claim 1, wherein said array into which said plurality of electrodes are configured comprises a two dimensional (2D) array.

7. The apparatus of claim 1, wherein said apparatus comprises a spatial array of PMUTs which are utilized with the delay control circuits for enabling transmitter beam forming, or receiver beam-steering, or a combination of transmitter beam forming and receiver beam-steering.

8. The apparatus of claim 1, wherein said ultrasonic transmitter/receiver apparatus is configured for use with, integration with, or integration within, a portable electronic device.

9. The apparatus of claim 1, wherein said apparatus is configured for measuring fat and muscle thickness at a particular human body part.

10. The apparatus of claim 9, wherein said apparatus is configured for measuring blood-flow and blood-pressure.

11. The apparatus of claim 1, wherein each of said piezoelectric micro-machined ultrasonic transducers (PMUTs) are formed over a cavity region within a material substrate, with a single electrode of said plurality of electrodes disposed over the piezo-electric micro-machined ultrasonic transducer (PMUT) over each said cavity region.

12. The apparatus of claim 1, wherein said charge pump comprises a series-parallel charge-pump having multiple stages which are driven by a non-overlapping clock generator, and wherein each of said multiple stages comprises high voltage switches, flying capacitors, and a storage capacitor.

13. The apparatus of claim 12, wherein said non-overlapping clock generator is configured to generate non-overlapping high-voltage clocks to operate each of the stages of said charge pump.

14. An ultrasonic transmitter/receiver apparatus, comprising:
   (a) an ultrasonic imaging array comprising a plurality of micro-machined ultrasonic transducers (MUTs), each comprising:

(i) a first electrode layer comprising a plurality of electrodes configured in an array;

(ii) a piezoelectric layer adjacent the first electrode layer; and (iii) a second electrode layer adjacent the piezoelectric layer;

(iv) wherein each said MUT is configured with a transmitting mode for generating acoustic pressure, and a receiving mode for sensing acoustic pressure; and (b) a control circuit structure, coupled to the ultrasonic imaging array, with said control circuit is configured for controlling said generation of acoustic pressure, controlling receiving information on acoustic pressure, and processing configured for analyzing said acoustic pressure information to generate physiological measurements;

(c) wherein said control structure comprises an application specific circuit having a charge pump and an array of channel circuits each configured for interfacing with channels within said ultrasonic imaging array;

(d) wherein each said channel circuit is configured to generate an output to a an analog-to-digital converter of a receiver whose output is directed to a processing element configured for processing ultrasonic data from said ultrasonic imaging array to generate image data which can be processed and directed to a display;

(e) wherein each channel circuit comprises a high voltage level shifter, a delay control circuit, and a transmit/receive switch;

(f) wherein each channel circuit is configured to receive a high voltage output from the charge pump which is applied to said high-voltage level-shifter in the channel circuit, said high-voltage level-shifter is configured for outputting a level-shifted output of sufficient voltage to drive channels in said ultrasonic imaging array;

(g) wherein said delay control circuit is configured for receiving a low-voltage pulse input from said control circuit and delaying it by a determined amount in each channel circuit before an output is generated to drive said high voltage level shifter; and (h) wherein said transmit/receive switch is configured for isolating the receiver from high transmit voltages generated during transmission.

15. The apparatus of claim 14, wherein said MUTs comprise either piezoelectric micro-machined ultrasonic transducers (PMUTs), or capacitive micro-machined ultrasonic transducers (CMUTs).

16. The apparatus of claim 14, wherein said physiological measurements are selected from the group of physiological measurements consisting of: body fat thickness measurement, muscle thickness measurement, blood-flow measurement, blood-pressure measurement, and ultrasonic imaging.

17. The apparatus of claim 14, wherein the application specific integrated circuit (ASIC) having a plurality of channels each with a delay control unit the high-voltage level-shifter and the charge pump which is configured to supply high-voltage to the high-voltage level-shifter for the transmitting mode, wherein when transmitting, an input low-voltage signal directed into each channel is delayed by an amount determined by delay control unit, and wherein the delayed signal is then level-shifted by high-voltage level shifters to drive the electrode array; and a receive/transmit switch configured to isolate the high voltage used in the transmitting mode from components used during the receiving mode.

18. The apparatus of claim 14, wherein said array into which said plurality of electrodes are configured comprises a two dimensional (2D) array.

19. The apparatus of claim 14, wherein said apparatus comprises a spatial array of MUTs which are utilized with the delay control circuits for enabling transmitter beam forming, or receiver beam-steering, or a combination of transmitter beam forming and receiver beam-steering.

20. The apparatus of claim 14, wherein said ultrasonic transmitter/receiver apparatus is configured for use with, integration with, or integration within, a portable electronic device.

21. The apparatus of claim 20, wherein said apparatus is configured for measuring blood-flow and blood-pressure.

22. The apparatus of claim 14, wherein said apparatus is configured for measuring fat and muscle thickness at a particular human body part.

23. The apparatus of claim 14, wherein each of said micro-machined ultrasonic transducers (MUTs) are formed over a cavity region within a material substrate, with a single electrode of said plurality of electrodes disposed over the micro-machined ultrasonic transducer (MUT) over each said cavity region.

24. The apparatus of claim 14, wherein said charge pump comprises a series-parallel charge-pump having multiple stages which are driven by a non-overlapping clock generator, and wherein each of said multiple stages comprises high voltage switches, flying capacitors, and a storage capacitor.

25. The apparatus of claim 24, wherein said non-overlapping clock generator is configured to generate non-overlapping high-voltage clocks to operate each of the stages of said charge pump.

* * * * *